(12) United States Patent
Maio et al.

(10) Patent No.: US 6,660,253 B2
(45) Date of Patent: Dec. 9, 2003

(54) SOLID LIGHT MOULDABLE MAKE-UP PRODUCT

(75) Inventors: Giuseppe Maio, Zelo Surrigone (IT); Antonio Mandelli, Cernusco Sul Naviglio (IT); Katya Spera, Monza (IT)

(73) Assignee: Intercos Italia S.p.A. (IT)

( * ) Notice: Subject to any disclaimer, the term of this patent is extended or adjusted under 35 U.S.C. 154(b) by 0 days.

(21) Appl. No.: 10/058,496

(22) Filed: Jan. 28, 2002

(65) Prior Publication Data

US 2002/0141958 A1 Oct. 3, 2002

(30) Foreign Application Priority Data

Jan. 30, 2001 (IT) .................. MI2001A000162

(51) Int. Cl.⁷ .................. A61K 7/021; A61K 9/14; A61K 9/50
(52) U.S. Cl. .................. 424/63; 424/489; 424/501
(58) Field of Search .................. 424/401, 63, 489, 424/501

(56) References Cited

U.S. PATENT DOCUMENTS 5,420,218 A * 5/1995 Toribuchi et al. ........... 526/214
5,866,108 A 2/1999 LeBras et al.
6,010,709 A * 1/2000 Nichols ................... 424/401

FOREIGN PATENT DOCUMENTS

| EP | 1036553 A2 | 9/2000 |
| JP | 2000212022 | 8/2000 |
| JP | 2001213727 | 8/2001 |
| WO | WO-9704737 A | 2/1997 |
| WO | WO-9856343 A | 12/1998 |
| WO | WO-0170186 A | 9/2001 |

* cited by examiner

*Primary Examiner*—Thurman K. Page
*Assistant Examiner*—Humera N. Sheikh
(74) *Attorney, Agent, or Firm*—Akerman Senterfitt

(57) ABSTRACT

The present invention refers to a solid light and mouldable cosmetic product in particular for make-up.

In an embodiment the make-up product comprises: from 10% to 90% of a powder phase; from 1% to 30% of a binder phase; from 40% to 90% of a water phase; from 1% to 50% of an absorbing polymer; said absorbing polymer is chosen so that said make-up product, after drying, has a specific weight comprised between 0.3 and 0.7.

26 Claims, No Drawings

SOLID LIGHT MOULDABLE MAKE-UP PRODUCT

The present invention refers to a solid light and mouldable cosmetic product in particular for make-up.

Solid make-up products, used mostly with the purpose of enhancing the aesthetic appearance of the epidermis, are generally made up of a set of powders (solid phase), that are bound by a group of substances, generally organic ones (binder phase), in order to attain the cohesion of the components so as to make them suitable for the applications, while providing at the same time the adherence of the coating and possibly curing principles to the epidermis.

Due to the strongly dissimilar nature of the solid and binder phase, from a chemical-physical point of view, and for the need to obtain the desirable make-up effect during its applications, the balance of the components is generally unstable and it strongly conditions both the preparation technologies as well as the presentation effects, by making it essential to use supports, thus causing the impossibility to handle directly the products and therefore making an external element (for instance brush, puff, etc.) essential for taking it and for its even distribution.

In the same way there is a difficulty in reaching certain locations of the epidermis with a risk to put in contact particularly sensitive regions with the materials forming the make-up.

An object of the present invention is to provide a make-up product that is light and easily applicable.

Another scope of the present invention is to provide a make-up product that is mouldable at will during the stage of production.

An additional scope of the present invention is to provide a resistant make-up product that can be used directly without any applicator.

According to the present invention, these and other objects are attained by means of a solid make-up product comprising: from 10% to 90% of a powder phase; from 1% to 30% of a binder phase; from 40% to 90% of a water phase; from 1% to 50% of an absorbing polymer; said absorbing polymer is chosen so that said make-up product, after drying, has a specific weight comprised between 0.3 and 0.7.

Such objects are also attained by means of a solid make-up product comprising: from 10% to 90% of a powder phase; from 1% to 30% of a binder phase; from 40% to 90% of a water phase; from 1% to 50% of a polymer of the allyl methacrylate family.

In addition such objects are attained by means of a preparation process for a solid make-up product comprising the stages: to prepare a powder phase; to prepare a binder phase; to prepare a phase water; to mix said powder phase and said binder phase so as to form a first compound; to mix said first compound with said water phase so as to form a second compound; to place said second compound into a porous container for a pre-established time; to dry the compound thus obtained in an oven for a time necessary to form a reticulated solid mass; to give shape to the product by means of appropriate cutting means in order to obtain the desired shapes.

Owing to the present invention it is possible to provide a bulky solid make-up product that because of the particular nature of its formulation gives the advantage to provide the components with consistency, compactness and lightness due to the low specific weight and as a consequence an extreme mouldability of the finished products, thus facilitating the operations of application on the epidermis and the topically repeated use for possible touch-ups. It results easily mouldable by means of cutting operations, thus allowing to obtain appropriate shapes so that it can be used without any applicator, and directly by handling it. For instance it could be shaped in bars, sticks, pyramids, ovoids and in other functional shapes for its direct use, thus offering at the same time the advantage to design packagings that are not conditioned by the relative embrittlement of the product any more. In particular the products can acquire any shape that one can imagine for use and decoration functionality, as compared with the products that are currently in use.

The characteristics and the advantages of the present invention will become evident from the following detailed description that is herein reported together with some embodiments of the make-up product according to the present invention, that are illustrated as non-limiting examples.

The present invention refers to a make-up product characterised by a composition comprising an absorbing polymer that is capable to absorb water by a weight greater than approximately 8–10 times its own weight, for instance a polymer of the allyl methacrylate family. Such composition allows to obtain a product having a specific weight comprised between 0.3 and 0.7 and more preferably between 0.4 and 0.6, as referred to the water at 25° C.

The composition according to the present invention comprises before drying:

- from 10% to 90%, preferably from 25% to 40%, of a powder phase;
- from 1% to 30 preferably from 2% to 10 of a binder phase;
- from 40% to 90%, preferably from 70% to 80%, of a water phase;
- from 1% to 50%, preferably from 1% to 10%, of an absorbing polymer.

The absorbing polymer is preferably a polymer of the allyl methacrylate family.

The powder phase comprises excipients and pigments. The excipients comprise elements or combinations of elements chosen among talc, mica, spherical and non-spherical silica, alluminum silicate and the pigments comprise elements or combinations of elements chosen among titanium dioxide, zinc oxide, iron oxide, hydrate chromium oxide, coated and non-coated, mica pearl, synthetic fluorophlogopite, calcium borum silicate, sodium borum silicate, preservatives.

The binder phase can preferably comprise elements or combinations of elements chosen among magnesium alluminum silicate, stearalkonium hectorite, quaternium-18 hectorite, hydroxyethylcellulose, carboxymethylcellulose, sodium magnesium silicate, synthetic calcium sulphate, solum follonum, vegetables and silicon oils, lipo-philic active principles, fragrances.

The water phase comprises water, and in addition it can comprise elements or combinations of elements chosen among polyacrylamide/$C_{13-14}$ isoparaffin/laureth-7, polysorbate-20, hydrophilic active principles.

In addition the make-up product can additionally comprise elements or combinations of elements chosen among polymethalcrilate, HDI (hexamethylene diisocianate), trimethylol hexyllactone crosspolymer, vinyl dimethicone, trimethylol hexyllactone crosspolymer, vinyl dimethicone, methicone silsesquioxane crosspolymer, nylon, polystyrene, dimethicone vinyldimethicone crosspolymer, as elements suitable to provide particular finish characteristics to the finished product.

For instance, the powder phase can contain elements suitable to give elasticity to the finished product in amounts comprised between 10% and 50%. To this purpose elements or combination of elements can be used that are chosen among talc, dimethicone/vinyldimethicone crosspolymer.

The process for the preparation of the make-up product, according to the present invention, provides the mixing, in an appropriate mixer, of the absorbing polymer, the excipients, the pigments and the binder phase.

The mixture thus obtained is added to the water phase by using, preferably, the technique called slurry (formation of a powder/solvent mixture that is kept in agitation). A suspension is thus formed that is kept in agitation with the aim of obtaining a homogenous dispersion. Other methods of mixing can be used.

The compound is then put into appropriate porous/filtering containers for a pre-established time, with the aim of expelling (partially) the liquids, subsequently it is submitted to drying in oven at a temperature comprised between 60° C. and 80° C. for the time necessary to form a reticulated solid mass. In this way the water that is present in the mixture is made evaporate in a time comprised between 12 and 48 hours and bars of dry product or also called "mother-moulds" are obtained. In particular, after drying bars are obtained that have a residual humidity between 1% and 5%. These bars are subsequently shaped with a variety of tools that are suitable to cut and to carve the desired final shapes, for instance such as diamond wire saw, laser, mill, high pressure air and/or water jet or else.

The use of an absorbing polymer such as allyl methacrylate, in combination with clays and the other ingredients, allowed to obtain a very light product, easily mouldable at will through cutting operations. It therefore becomes possible to provide a cosmetic make-up product with the most various shapes (bars, pyramids, stars, ovoid shapes, etc). In addition to the particular physical property an attractive and pleasant appearance has been obtained that is due, not to the packaging, but to the product itself and to the shapes in which it can be marketed.

Some embodiments of the make-up product according to the present invention, that are illustrated as non limiting examples are reported herein.

EXAMPLE N. 1

| Formula 1 | % slurry | % on dry |
|---|---|---|
| HDI/trimethylol hexyllactone crosspolymer | 5.70 | 20.00 |
| Vinyldimethicone/methicone silsequioxane crosspolymer | 2.90 | 10.30 |
| Talc | 5.50 | 19.20 |
| Preservatives | 0.30 | 1.00 |
| Amorphous silica | 0.50 | 1.70 |
| Iron oxide brown | 0.09 | 0.30 |
| Iron oxide yellow | 0.50 | 1.70 |
| Iron oxide red | 0.07 | 0.20 |
| Iron oxide black | 0.03 | 0.10 |
| Mica, titanium dioxide | 0.85 | 3.00 |
| Polymethyl methacrylate | 0.60 | 2.10 |
| Octyldodecyllactate | 0.53 | 1.90 |
| Allyl methacrylates crosspolymer | 4.30 | 15.00 |
| Solum fullonum | 4.30 | 15.00 |
| Synthetic calcium sulphate | 2.00 | 7.00 |
| Water | 71.40 | 0.00 |
| Polyacrylamide, C13–14 isoparaffin, laureth-7 | 0.43 | 1.50 |
| TOTAL | 100 | 100 |

EXAMPLE N. 2

| Formula 2 | % slurry | % on dry |
|---|---|---|
| HDI/trimethylol hexyllactone crosspolymer | 3.70 | 11.70 |
| Vinyldimethicone/methicone silsequioxane crosspolymer | 1.80 | 5.70 |
| Talc | 3.00 | 9.50 |
| Preservatives | 0.30 | 0.95 |
| Amorphous silica | 0.30 | 0.95 |
| Mica, titanium dioxide, iron oxide | 5.80 | 18.40 |
| Mica, iron oxide | 5.80 | 18.40 |
| Mica, titanium dioxide | 0.60 | 1.90 |
| Polymethyl methacrylate | 0.42 | 1.30 |
| Octyldodecyllactate | 0.25 | 0.80 |
| Allyl methacrylates crosspolymer | 3.70 | 11.70 |
| Solum fullonum | 3.70 | 11.70 |
| Calcium sulphate | 1.80 | 5.70 |
| Water | 68.43 | 0.00 |
| Polyacrylamide, $C_{13-14}$ isoparaffin, laureth-7 | 0.40 | 1.30 |
| TOTAL | 100.00 | 100.00 |

EXAMPLE N. 3

| Formula 3 | % slurry | % on dry |
|---|---|---|
| Talc | 12.78 | 43.08 |
| Dimethicone/vinyldimethicone crosspolymer | 1.69 | 5.69 |
| Preservatives | 0.30 | 1.00 |
| Magnesium aluminium silicate | 2.20 | 7.41 |
| Iron oxide brown | 0.40 | 1.35 |
| Iron oxide yellow | 1.53 | 5.20 |
| Iron oxide red | 0.60 | 2.02 |
| Solum fullonum | 4.00 | 13.48 |
| Allyl methacrylates crosspolymer | 4.68 | 15.77 |
| Stearalkonium hectorite | 1.50 | 5.00 |
| Water | 70.32 | 0.00 |
| TOTAL | 100.00 | 100.00 |

EXAMPLE N. 4

| Formula 4 | % slurry | % on dry |
|---|---|---|
| Preservatives | 0.20 | 0.60 |
| Polysorbate-20 | 0.79 | 2.59 |
| Allyl methacrylates crosspolymer | 5.15 | 16.84 |
| Solum follonum | 2.48 | 8.11 |
| Water | 69.40 | 0.00 |
| Magnesium aluminium silicate | 1.20 | 3.93 |
| Mica, titanium dioxide, iron oxide | 2.48 | 8.11 |
| Mica, titanium dioxide | 7.90 | 25.82 |
| Talc | 6.10 | 19.94 |
| Dimethicone/vinyldimethicone crosspolymer | 0.90 | 2.95 |
| Synthetic calcium sulphate | 2.50 | 8.16 |
| Sodium magnesium silicate | 0.90 | 2.95 |
| TOTAL | 100.00 | 100.00 |

EXAMPLE N. 5

| Formula 5 | % slurry | % on dry |
|---|---|---|
| Preservatives | 0.20 | 0.70 |
| Polysorbate-20 | 0.80 | 2.70 |
| Allyl methacrylates crosspolymer | 5.20 | 17.30 |
| Solum follonum | 2.50 | 8.30 |

-continued

| Formula 5 | % slurry | % on dry |
|---|---|---|
| Water | 70.00 | 0.00 |
| Magnesium aluminium silicate | 1.20 | 4.00 |
| Iron oxide red | 2.60 | 8.70 |
| Iron oxide brown | 0.60 | 2.00 |
| Titanium dioxide | 1.40 | 4.70 |
| Talc | 13.25 | 44.10 |
| Dimethicone/vinyldimethicone crosspolymer | 1.65 | 5.50 |
| Calcium sulphate | 0.60 | 2.00 |
| TOTAL | 100.00 | 100.00 |

What is claimed is:

1. A solid make-up product comprising:
    from 10% to 90% of a powder phase;
    from 1% to 30% of a binder phase;
    from 40% to 90% of a water phase;
    from 1% to 50% of an absorbing polymer:
    wherein the absorbing polymer is an allyl methacrylate polymer; and
    wherein said absorbing polymer is chosen so that said make-up product, after drying, has a specific weight per unit volume of between 0.3 and 0.7.

2. Solid make-up product according to claim 1 wherein said absorbing polymer is capable of absorbing water by a weight 8 times greater than its own weight.

3. Solid make-up product according to claim 1 wherein said absorbing polymer comprises an allyl methacrylate crosspolymer.

4. Solid make-up product according to claim 1 comprising from 25% to 40% of the powder phase.

5. Solid make-up product according to claim 1 comprising from 2% to 10% of the binder phase.

6. Solid make-up product according to claim 1 comprising from 70% to 80% of the water phase.

7. Solid make-up product according to claim 1 comprising from 1% to 10% of the absorbing polymer.

8. Solid make-up product according to claim 1 wherein said specific weight per unit volume is between 0.4 and 0.6.

9. Solid make-up product according to claim 1 wherein said powder phase comprises excipients and pigments.

10. Solid make-up product according to claim 9 wherein said excipients comprise elements or combinations of elements chosen among talc, mica, spherical and non-spherical silica, and aluminum silicate.

11. Solid make-up product according to claim 9 wherein said pigments comprise elements or combinations of elements chosen among titanium dioxide, zinc oxide, iron oxide, hydrate chromium oxide, coated and non-coated, mica pearl, synthetic fluorophlogopite, calcium borum silicate, sodium borum silicate, preservative.

12. Solid make-up product according to claim 1 wherein said binder phase comprises elements or combinations chosen among magnesium aluminum silicate, stearalkonium hectorite, quaternium-18 hectorite, hydroxyethylcellulose. carboxymethylcellulose, sodium magnesium silicate, calcium sulfate, solum fullonum, vegetables and silica oils, lipophilic active principles.

13. Solid make-up product according to claim 1 wherein said water phase comprises elements or combinations of elements chosen among water, polyacrylamide/$C_{13-14}$ isoparaffin/laureth-7, polysorbate-20 hydrophilic active principles.

14. Solid make-up product according to claim 1 further comprising elements or combinations of elements chosen among polymethalcrilate, HDI, trimethylol hexyllactone crosspolymer, vinyl dimethicone, methicone silsesquioxane crosspolymer, nylon, polystyrene, dimethicone vinyldimethicone crosspolymer.

15. Solid make-up product according to claim 1 wherein said powder phase comprises elements suitable to give elasticity to said make-up product in an amount comprising between 10% and 50%.

16. Solid make-up product according to claim 15 wherein said elements suitable to give elasticity to said make-up product include elements or combinations of elements chosen among talc, and dimethicone/vinyldimethicone crosspolymer.

17. Solid make-up product comprising: from 10% to 90% of a powder phase; from 1% to 30% of a binder phase; from 40% to 90% of a water phase; from 1% to 50% of an allyl methacrylate crosspolymer.

18. Process for the preparation of a solid make-up product comprising the steps:
    preparing a powder phase;
    preparing a binder phase;
    preparing a water phase;
    mixing said powder phase and said binder phase with an allyl methacrylate absorbing polymer so as to form a first compound;
    mixing said first compound with said water phase so as to form a second compound;
    placing said second compound in a porous container for pre-established time;
    drying the compound thus obtained in an oven for the time necessary to form a reticulated solid mass;
    shaping the make-up product by means of appropriate cuffing means in order to obtain the desired shapes.

19. Solid make-up product according to claim 1, wherein said make-up product, after drying, is a solid, moldable product having a humidity between 1% and 5%.

20. Process according to claim 18 wherein the drying step is carried out to form a reticulated solid mass having a humidity between 1% and 5%.

21. Process according to claim 18 wherein the absorbing polymer absorbs water by a weight 8 times greater than its own weight.

22. Process according to claim 18 wherein the powder phase it added in an amount to form 25% to 40% of the make-up product.

23. Process according to claim 18 wherein the binder phase is added in an amount to form 2% to 10% of the make-up product.

24. Process according to claim 18 wherein the water phase is added in an amount to form 70% to 80% of the make-up product.

25. Process according to claim 18 wherein the absorbing polymer is added in an amount to form 1% to 10% of the make-up product.

26. Process according to claim 18 wherein the make-up product comprises from 10% to 90% of the powder phase; from 1% to 30% of the binder phase; from 40% to 90% of the water phase; and from 1% to 50% of the allyl methacrylate crosspolymer.

* * * * *

UNITED STATES PATENT AND TRADEMARK OFFICE
CERTIFICATE OF CORRECTION

PATENT NO. : 6,660,253 B2
DATED : December 9, 2003
INVENTOR(S) : Giuseppe Maio, Antonio Mandelli and Katya Spera It is certified that error appears in the above-identified patent and that said Letters Patent is hereby corrected as shown below:

Column 2,
Line 30, replace "30" with -- 30% --
Line 30, replace "10" with -- 10% --

Column 5,
Line 58, replace "hydroxyethylcellulose." with -- hydroxyethylcellulose, --

Column 6,
Line 37, replace "cuffing" with -- cutting --

Signed and Sealed this

Twenty-eighth Day of December, 2004

JON W. DUDAS
*Director of the United States Patent and Trademark Office*